United States Patent [19]
van Nassau et al.

[11] Patent Number: 4,540,813
[45] Date of Patent: Sep. 10, 1985

[54] PROCESS FOR THE PREPARATION OF UREA

[75] Inventors: Petrus J. M. van Nassau, Munstergeleen; Andreas J. Biermans, Urmond; Kees Jonckers, Born; Mario G. R. T. de Cooker, Beek, all of Netherlands

[73] Assignee: Unie van Kunstmestfabrieken B.V., Utrecht, Netherlands

[21] Appl. No.: 496,317

[22] PCT Filed: Aug. 31, 1982

[86] PCT No.: PCT/EP82/00188
§ 371 Date: May 2, 1983
§ 102(e) Date: May 2, 1983

[87] PCT Pub. No.: WO83/00862
PCT Pub. Date: Mar. 17, 1983

[30] Foreign Application Priority Data

Sep. 1, 1981 [NL] Netherlands .......... 8104040

[51] Int. Cl.³ .......... C07C 126/02
[52] U.S. Cl. .......... 564/71; 564/70
[58] Field of Search .......... 564/70, 71

[56] References Cited

U.S. PATENT DOCUMENTS

| | | | |
|---|---|---|---|
| 3,120,563 | 2/1964 | Bongard | 564/70 |
| 3,406,201 | 10/1968 | Baumann et al. | |
| 3,759,992 | 9/1973 | Mavrovic | 564/71 |
| 3,957,868 | 5/1976 | Verstegen | 564/71 |
| 4,066,693 | 1/1978 | Venderbos | 564/70 |
| 4,115,449 | 9/1978 | Biermans et al. | 564/70 |
| 4,173,615 | 11/1979 | Otsuka et al. | |
| 4,301,299 | 11/1981 | Inoue et al. | 564/70 |
| 4,354,040 | 10/1982 | Inoue et al. | 564/70 |

FOREIGN PATENT DOCUMENTS

1124868  8/1968  United Kingdom .
1147734  4/1969  United Kingdom .

Primary Examiner—Charles F. Warren
Assistant Examiner—R. A. Picard
Attorney, Agent, or Firm—Cushman, Darby & Cushman

[57] ABSTRACT

A process for the preparation of urea from ammonia and carbon dioxide at an elevated temperature and pressure having a reaction zone and a stripping zone. In the reaction zone, carbon dioxide and a portion of the ammonia are converted to ammonium carbamate, and a portion of the ammonium carbamate is converted to urea, the combined conversions resulting in a net formation of heat. In the stripping zone, a urea product stream containing unconverted ammonium carbamate is heated by heat exchange with the reaction zone to decompose a portion of the ammonium carbamate. In the reaction zone, the conversion of ammonium carbamate into urea is continued until the quantity of urea formed is at least 50 percent of that quantity of urea that would be obtained at equilibrium under the reaction conditions present in the reaction zone.

14 Claims, 3 Drawing Figures

PROCESS FOR THE PREPARATION OF UREA

This invention relates to a process for preparing urea from ammonia and carbon dioxide at elevated temperatures and pressures whereby the net heat produced by the urea synthesis reaction can be more efficiently and effectively utilized.

One process for the preparation of urea which has found wide use in practical applications is described in European Chemical News Urea Supplement of Jan. 17, 1969, at pages 17–20. In the process there disclosed, the urea synthesis solution is formed in a reaction zone maintained at a high pressure and temperature, and is thereafter subjected to a stripping temperature at the synthesis pressure by heating this solution and contacting it countercurrently with a carbon dioxide stripping gas so as to decompose a major portion of the ammonium carbamate contained therein. The gas mixture thus formed, containing ammonia and carbon dioxide together with the stripping gas and a small quantity of water vapor, is removed from the remaining urea product stream and introduced into a condensation zone wherein it is condensed to form an aqueous ammonium carbamate solution. This aqueous carbamate solution, as well as the remaining non-condensed gas mixture, is recycled to the reaction zone for conversion to urea. The condensation of this gas mixture returned to the reaction zone provides the heat required for the conversion of ammonium carbamate into urea, and no heat need be supplied to the reaction zone from the outside.

The heat required for the stripping treatment is provided by the condensation of high-pressure steam on the outside of tubes in a vertical heat exchanger in which the stripping takes place. According to this publication, approximately 1,000 kg of steam at a pressure of about 25 bar is required per ton of urea. In practice, the consumption of high pressure steam (25 bar) has been reduced to about 850 kg per ton of urea, and the heat used in the stripping treatment can be partially recovered by condensation of the resulting gas mixture. This condensation, however, takes place at a relatively low temperature level with the result that steam of only 3-5 bar is produced, for which there is relatively little use in either this process or outside the process. For this reason, and particularly in view of continually increasing energy prices, it is highly desirable to reduce the consumption of high-pressure steam as much as possible and, depending on local conditions and needs, it may be desirable as well to avoid or greatly reduce the production of surplus low-pressure steam.

Various proposals have already been made to use the heat released in the formation of carbamate from ammonia and carbon dioxide to provide at least a part of the heat requirements in the stripping treatment. For various reasons, however, these proposals have not found practical application. For example, in British patent specification No. 1,147,734, a process is disclosed wherein the ammonium carbamate and urea synthesis is effected in two successive reaction zones. Fresh ammonia and at least a portion of the fresh carbon dioxide are fed into the first reaction zone, and the heat released by the formation of ammonium carbamate in this first reaction zone is transferred, via builtin heat exchange elements, to the urea synthesis solution formed in the second reaction zone at a pressure equal to or lower than that in the first reaction zone, resulting in the decomposition of unreacted ammonium carbamate. The decomposition products thus formed are stripped from the remaining urea solution by means of an inert gas.

In carrying out this known process, the fresh ammonia and carbon dioxide must be pre-heated to a high temperature, for instance to the synthesis temperature maintained in the first reaction zone, in order to have sufficient heat to effect the decomposition of ammonium carbamate in the stripping zone. This pre-heating of the reactants consumes a significant quantity of high-pressure steam. Of the surplus heat formed in the urea synthesis, however, only a small portion can be recovered as steam at a pressure of about 5 bar via a cooling system for the second reaction zone. A larger portion of this surplus heat is recovered at a relatively low temperatures level in the absorption column, operating at the pressure of the second reaction zone, in which column the ammonia and carbon dioxide stripped from the urea product stream are separated from the inert stripping gas. The steam so produced has a relatively low pressure of only about 2 bar, for which there is little use within the process.

In another process as disclosed in U.S. Pat. No. 3,957,868, the urea synthesis reaction is carried out in the shell side of a vertical tubular heat exchanger wherein the tops of the tubes open into the shell-side space of the heat exchanger. The urea synthesis solution formed in the shell-side reaction zone flows into and down the inside of the tubes wherein ammonium carbamate is decomposed by means of the heat of reaction transferred through the tube walls, and the ammonia and carbon dioxide thus released are stripped from the solution.

In order to maximize the decomposition of ammonium carbamate, it is necessary to have the heat of reaction available at as high a temperature level as possible, and to insure optimum heat transfer to the solution to be stripped. The measures proposed in this reference to accomplish this include carrying out the urea synthesis and the stripping at a temperature of 210° to 245° C. and a pressure of 250 to 600 atmospheres, maintaining a relatively high $NH_3/CO_2$ molar ratio in the liquid phase in the reaction zone, and recirculating a part of the gas mixture removed from the stripping zone into the bottom of the reaction zone together with an extra quantity of gas mixture which is kept available for recirculation by condensing only a portion of the gaseous ammonia and carbon dioxide supplied to the reaction zone to ammonium carbamate. Thus, the weight of urea produced will be low relative to the quantities of ammonia and carbon dioxide supplied to the reaction zone.

Because of the high temperatures employed in this process, the materials of construction to be used must satisfy high standards of corrosion resistance. Moreover, a relatively high capital investment is required for the equipment because of the higher pressure used, and the special design of the combined reactor-stripper. When all of these factors are taken into account, this known process, in practical application, has little or no economic advantage over the process described in the European Chemical News Urea Supplement which has found general application.

It is an object of the present invention to provide a process for the production of urea wherein the quantity of high-pressure steam required for the decomposition of non-converted ammonium carbamate is substantially reduced while avoiding the disadvantages of the above-mentioned known processes.

In accordance with the invention, the condensation of ammonia and carbon dioxide in the reaction zone is effected in the presence of relatively large quantities of urea and water, which causes the average temperature in the reaction zone to rise considerably. The heat of reaction from the reaction zone is exchanged with the stripping zone wherein it is utilized to decompose ammonium carbamate in the product stream. When carried out according to the invention the heat of reaction from the reaction zone is available at a high temperature level and can be more effectively and efficiently utilized than in the prior art in the decomposition and stripping of ammonium carbamate in the urea product stream.

Specifically, the invention relates to a process for preparing urea from carbon dioxide and an excess amount of ammonia at an elevated temperature and pressure, wherein at least a part of the urea synthesis is effected in a reaction zone which is in heat exchange with a stripping zone wherein ammonium carbamate is decomposed and the decomposition products are removed from a urea product stream, and the stripped urea product stream is processed to a urea solution or solid urea. In accordance with the present invention, the urea synthesis taking place in the reaction zone exchanging heat with the stripping zone is continued until the quantity of urea produced is at least 50 percent of the equilibrium quantity of urea obtainable under the reaction conditions prevailing in the reaction zone. Preferably, the urea synthesis in the reaction zone is continued to the point that the quantity of urea produced is at least 70 percent of that which would be formed at equilibrium.

In order to further increase and make maximum use of the heat released in this reaction zone, it is desirable to insure intensive mixing of the contents of the reaction zone, which has the effect of raising the temperature level and promotes an increased transfer of heat to the stripping zone. To this end, the stripping can be carried out in a known manner within the tubes of a vertical heat exchanger while the shell side of the exchanger serves as the reaction zone, and the contents of the reaction zone are sufficiently mixed so that the difference in temperature between the top and bottom of the reaction zone is limited to 5° C. at most. Preferably, to maximize the heat transfer, this temperature difference should be maintained at most at about 2° C.

Contrary to the above-noted process disclosed in U.S. Pat. No. 3,957,868, the present process accomplishes an effective and efficient exchange of heat from the reaction zone to the stripping zone without the need for extremely high pressures and temperatures, but rather under more usual urea synthesis pressure and temperature conditions, such as 125-250 bar and 170°-205° C., respectively. It is also possible when using this process to maintain the stripping zone and the reaction zone at the same pressure, although enhancement of the heat transfer and stripping effect may be realized by operating the stripping zone at a pressure lower than the reaction zone.

The amount of ammonium carbamate which is still present in the urea synthesis solution formed in the reaction zone can be decreased by using a large excess of ammonia and longer residence times, so that a larger proportion of the ammonium carbamate formed is converted to urea. This requires, however, a larger reaction zone per unit of urea capacity, which in view of the design capacities of modern urea synthesis plants of 1500-2000 tons per day or more, may give rise to constructional and logistic problems.

This dilemma can be avoided by permitting the urea synthesis solution formed in the reaction zone to continue reacting in a separate after-reaction zone until, depending on the reaction conditions employed, 90 to 97 percent of the equilibrium amount of urea that can be achieved under these conditions has been formed. Since the rate of conversion of carbamate to urea decreases as equilibrium is approached continuing the urea synthesis under the same conditions as used in the reaction zone would require a long residence time and therefore a large after-reaction zone. The additional cost could then outweigh the advantage of a small increase in the amount of urea produced. However by having the urea synthesis in the after-reaction zone, and possibly in the reaction zone as well, take place at a pressure which is higher than the pressure at which the stripping treatment takes place, the carbamate-urea equilibrium shifts toward the urea side with the result that the urea synthesis solution contains less carbamate that has to be decomposed. Even a small increase of pressure in the reaction zones will result in higher conversion, but if a higher pressure is used in the after-reaction zone than in the reaction zone, a pressure differential of 10 bar or more is advisable. In that case, a pressure of 125-150 bar is preferably used in the reaction zone, and a pressure of 160-250 bar is preferably used in the after-reaction zone, and the stripping treatment can then take place at the pressure used in the reaction zone.

If the amount of heat available in the reaction zone for transfer to the stripping zone is insufficient, due to too low a temperature level, to achieve an acceptable level of carbamate decomposition and expulsion of the gases thus formed, the remaining urea product stream leaving the stripping zone, still containing ammonium carbamate, can be subjected to a second stripping treatment in which the heat required for decomposition of the carbamate is supplied by means of steam. This second stripping treatment can be effected at the pressure maintained in the first stripping treatment, or a lower pressure may be used. Alternatively, it is possible to treat only a portion of the urea synthesis solution in the stripping zone exchanging heat with the reaction zone, while the remainder is sent directly to a parallel stripping treatment wherein the heat is provided by steam. It is also possible to first strip the urea synthesis solution using steam heat and to subsequently introduce it into the stripping zone exchanging heat with the reaction zone.

When carrying out the preparation of urea in accordance with the invention, it is possible to increase the amount of heat exchanged from the reaction zone to the stripping zone by maintaining the pressure in the reaction zone higher than the stripping zone. As the pressure in the reaction zone increases, the condensation of carbon dioxide and ammonia to ammonium carbamate takes place at higher temperatures and, consequently, more heat will be available for the decomposition of carbamate in the stripping zone. Preferably, a pressure differential between the heat-exchanging reaction and stripping zones should be at least about 20 bar. On the other hand, a pressure difference of more than 120 bar, although theoretically possible, complicates the design of the reactor-stripper apparatus. Most preferably, the reaction zone should be maintained at a pressure of 40 to 60 bar higher than in the stripping zone. This provides a suitable driving force for the heat exchange without the need for equipment of a more complex design, and permits the compression of the gas released in the stripping zone to the reaction zone pressure without the need for intermediate cooling.

The invention will be explained in greater detail with reference to the attached drawings.

In each of the figures, the equipment identified with the letter A represents a reactor-stripper which is here illustrated, for example, as a vertical shell and tube heat exchanger wherein the shell side of the heat exchanger is the reaction zone and the tube side of the exchanger is the stripping zone. Furthermore, in each of the drawings, B represents a high pressure carbamate condenser, C represents an after-reactor, D represents a heater-decomposer, E represents a scrubber, F represents a carbon dioxide compressor, G represents an ammonia heater, H represents a gas ejector, K represents an ammonia pump, and L represents a carbamate pump.

Figure 1:
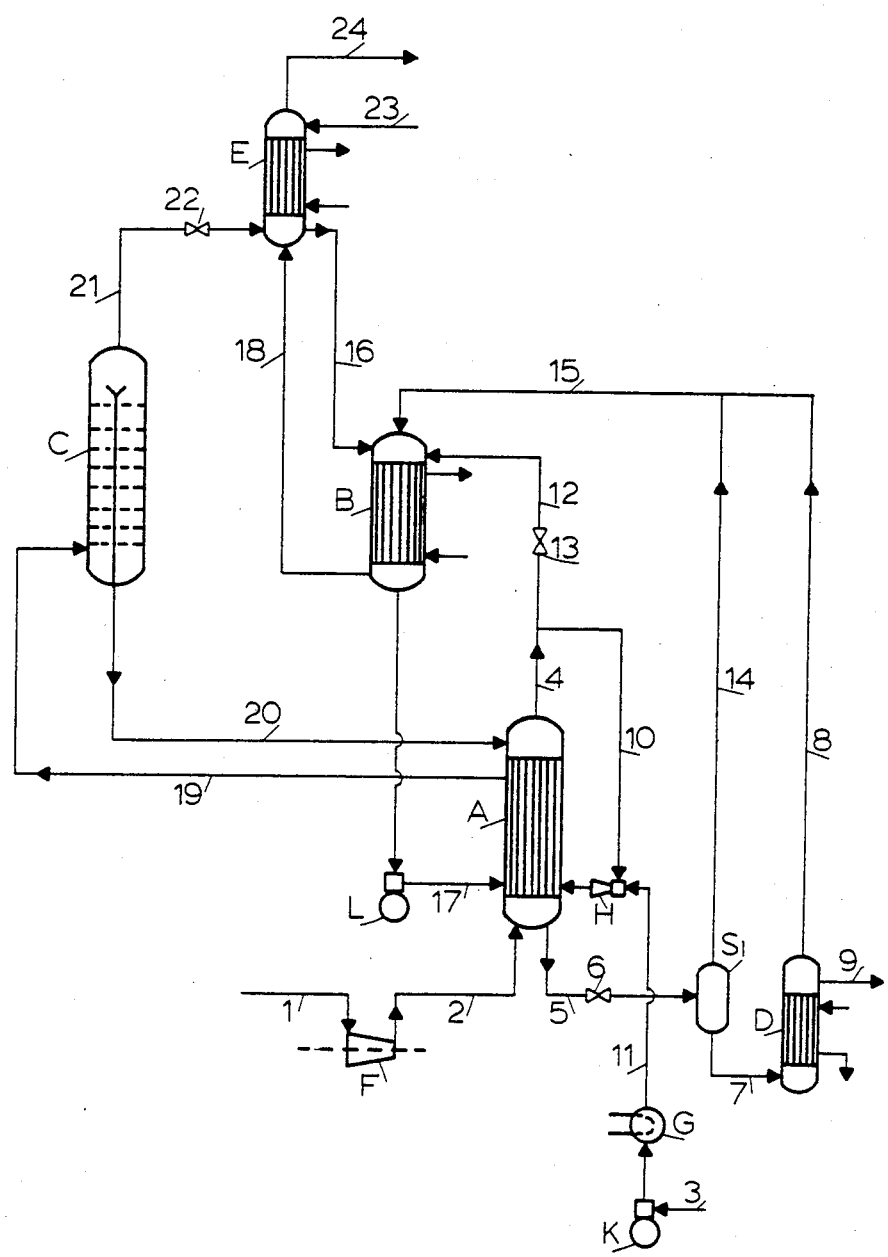
FIG. 1 illustrates an embodiment of the process according to the invention wherein the urea synthesis solution is stripped in two successive steps, the first stripping step deriving heat from heat exchange with the reaction zone, and the second deriving heat from steam.

Referring first to the embodiment illustrated in FIG. 1, the urea synthesis solution obtained from after-reactor C, which contains non-converted ammonium carbamate and free ammonia in addition to urea and water, is passed via line 20 into the stripping zone of reactor-stripper A wherein it is heated by heat exchange with the reaction zone and passed countercurrently against gaseous carbon dioxide. This carbon dioxide is introduced into the bottom of the stripping zone via line 1, carbon dioxide compressor F, and line 2 at a pressure of, for example, 240 bar. Air or some other oxygen-containing inert gas mixture is added to the carbon dioxide in order to maintain the stainless steel materials of construction contacting the carbamate-containing solutions at high temperatures in a passive state.

In the stripping zone, the heat derived from the reaction zone causes the decomposition of ammonium carbamate to form a gas mixture consisting of ammonia, carbon dioxide, and water vapor which is expelled from the urea synthesis solution by the stripping treatment, and, together with the freshly supplied carbon dioxide, is discharged from the stripping zone of reactor-stripper A through line 4. The residual solution containing product urea, which still contains an amount of ammonium carbamate, is discharged from the stripping zone through line 5, expanded in expansion valve 6 to a pressure of, for example, 140 bar or lower, and introduced into gas-liquid separator $S_1$ wherein a gas mixture of ammonia, carbon dioxide, and water vapor evolved from the expansion is separated from the remaining urea product solution. This remaining urea product is sent through line 7 to heater-decomposer D, here illustrated as a vertical tubular heat exchanger, in which heat is supplied by means of 20–25 bar steam. In heater-decomposer D, substantially all of the remaining ammonium carbamate still present in the urea product stream is decomposed into ammonia and carbon dioxide and, together with a small amount of water vapor, is discharged as a gas mixture through line 8. The urea product solution is discharged through line 9 after which it can be subjected to further known and customary treatments to form a concentrated urea solution or solid urea.

In the embodiment illustrated in FIG. 1, the urea product solution to be treated in the second stripping step is introduced into the bottom of heater-composer D and the solution and evolved gases flow through the tubes cocurrently. It is also possible to feed to urea solution to the heater from the top and to let it flow downward in the tubes, countercurrent to the expelled gases. In the latter case, the separation of the gas mixture released by the expansion in expansion valve 6 can take place in the head of heater-decomposer D, and a separate gas-liquid separator $S_1$ is not necessary.

A portion of the gas mixture discharged from the stripping section of reactor-stripper A through line 4 is led into the bottom of shell side of reactor-stripper A in which the reaction zone is located, via line 10 and ejector H. Ejector H is driven by fresh ammonia, which is supplied through line 3, brought to the desired pressure by pump K and the desired temperature in ammonia heater G and thereafter into ejector H through line 11.

The remaining part of the gas mixture discharged from the stripping zone through line 4 is introduced into carbamate condenser B via line 12 and expansion valve 13. Ammonium carbamate condenser B is maintained at the same pressure as heater-decomposer D. Carbamate condenser B is also fed, through lines 8 and 15, with the gas mixture expelled from heater-decomposer D and possibly, through lines 14 and 15, with the gas mixture separated from the urea solution in gas-liquid separator $S_1$, where the separator is employed. These gas streams fed to carbamate condenser B are partially condensed in the presence of the carbamate solution supplied through line 16 from scrubber E, and the heat of condensation can be recovered and used to produce steam of, for example, 3–6 bar. The carbamate solution thus formed is brought up to the pressure of the reaction zone by means of carbamate pump L, and is introduced via line 17 into the bottom of the reaction zone of reactor-stripper A. The non-condensed gas mixture from carbamate condenser B, which contains part of the inert gases introduced into the process with the fresh carbon dioxide and ammonia, flows to scrubber E through line 18.

In the reaction zone of reactor-stripper A, a large portion of the ammonia and carbon dioxide fed through lines 10 and 11 via ejector H is converted to ammonium carbamate, and a portion of this ammonium carbamate and the carbamate supplied from carbamate condenser B through carbamate pump L and line 17 are converted to urea and water. The condensation reaction forming ammonium carbamate is exothermic, forming an amount of heat, whereas the conversion of carbamate to urea and water is endothermic, consuming heat. However, a surplus of heat is produced by the combined reactions and is available for the decomposition of non-converted carbamate in the stripping zone of reactor-stripper A. By having the formation of carbamate take place in the presence of an amount of urea and water in accordance with the invention, a higher temperature is reached in the reaction zone, so that a greater portion of the surplus heat can be transferred to the stripping zone. This effect is already appreciable when, in the reaction zone, about one-half of the equilibrium amount of urea obtainable under the reaction conditions employed is formed, and the effect will be stronger as the urea conversion more closely approaches equilibrium. For instance, if in a typical embodiment of the process according to FIG. 1 at a pressure of about 240 bar, molar ratio of ammonia to carbon dioxide of 3.40:1 and a molar ratio of water to carbon dioxide of 0.46:1 about 50% of the equilibrium amount of urea is formed the average temperature in the reaction zone will be about 195° C. With 60, 70, 80 and 90% of the equilibrium amount of urea formed the temperature will be about 196°, 199°, 201° and 203° C., respectively. The temperature increases resulting from higher conversions of ammonium carbamate to urea and water are substantial with respect to the temperature differential across the heat exchange surfaces in the reactor-stripper. Preferably, the degree of conversion of carbamate to urea in the reaction zone will be selected to approach about 70 percent of equilibrium. Urea formation of more than 90 percent of the equilibrium amount, however, requires a considerably longer residence time due to the strongly decreasing reaction rate, and consequently requires an unattractively large volume in the reaction zone.

Given the pressure, the amount of excess ammonia, the molar ratio of $H_2O/CO_2$ and residence time, the temperature that can be reached in the reaction zone is fixed. Also, the amount of gas mixture that can be fed via ejector H is fixed, inasmuch as it affects the residence time, and thus the amount of heat transferred cannot be further increased by increasing the amount of this gas mixture. The heat that is not utilized is removed from the process by condensing part of the gas mixture removed from the stripping zone in carbamate condenser B and scrubber E, and by condensing part of the gas mixture discharged from the reaction zone in after-reactor C and scrubber E.

The contents of the reaction zone should be mixed intensively in order to achieve the most uniform heat distribution possible and to maximize the heat transfer to the stripping zone. Some mixing is achieved by having the gas mixture and the carbamate solution flow through the reaction zone from the bottom to the top. However, this mixing, and consequently the heat transfer to the stripping zone can be further improved by the installation of baffles, guide plates, or similar elements in the reaction zone.

The aqueous urea solution containing excess ammonia and ammonium carbamate formed in the reaction zone, together with the non-condensed gas, is sent via line 19 to after-reactor C, which is maintained at the same pressure as the reaction zone in reactor stripper A, and there the urea synthesis is continued until at least about 90 percent of the equilibrium amount of urea which can be obtained under the reaction conditions in the after-reactor has been formed. The heat required for this conversion of ammonium carbamate to urea is obtained by the formation of an additional quantity of ammonium carbamate in the after-reactor from the gaseous ammonia and carbon dioxide fed through line 19. The urea synthesis solution thereby obtained is then led via line 20 to the stripping zone of reactor-stripper A. The gas mixture leaving the top of after-reactor C, consisting of inert gases, ammonia, carbon dioxide, and water vapor, is sent via line 21 and expansion valve 22 to scrubber E, wherein the ammonia and carbon dioxide are recovered at the same pressure used in heater-decomposer D and carbamate condenser B by scrubbing with water or a dilute solution of ammonium carbamate supplied through line 23, while removing the heat of absorption. The residual off-gas mixture remaining after scrubber E is discharged through line 24, and the carbamate solution obtained in scrubber E is introduced into carbamate condenser B through line 16.

When carrying out the embodiment of the invention as illustrated in FIG. 1 and described above, a reduction in high-pressure steam consumption (25 bar) of about 10 percent relative to the process described in European Chemical News Urea Supplement and discussed above, can be achieved, the precise steam savings depending on the process conditions chosen. In this embodiment, the total amount of urea synthesis solution is treated in the stripping zone of reactor-stripper A. However, the amount of heat available for the stripping treatment is limited, so that only a relatively low stripping efficiency can be achieved, and a considerable amount of carbamate still remains to be decomposed and expelled in heater-decomposer D.

Figure 2:
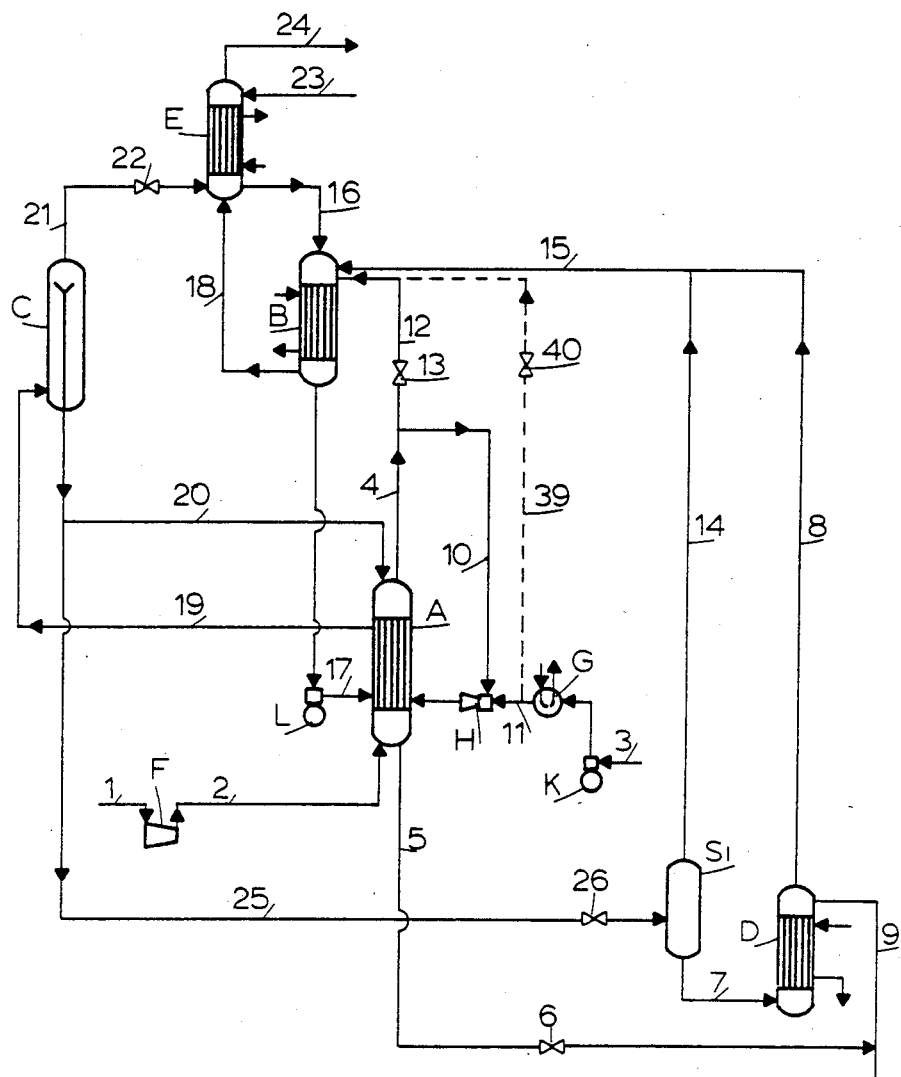
FIG. 2 illustrates an embodiment of the invention in which a portion of the urea synthesis solution is stripped utilizing heat derived from heat exchange with the reaction zone, and a remaining part of the urea synthesis solution is subjected to a separate stripping treatment wherein the heat is derived from steam.

In the embodiment illustrated in FIG. 2, the urea synthesis solution formed in after-reactor C is divided into two portions. One portion, for example 20 to 50 percent of the total amount, is fed to the stripping zone of reactor-stripper A through line 20, and the remaining portion, for example 50–80 percent of the total amount, is carried through line 25 to expansion valve 26 and thereafter to gas-liquid separator $S_1$ for removal of the gas mixture evolved during the expansion, and the remaining urea synthesis solution is introduced into heater-decomposer D. The quantity of the urea synthesis solution from after-reactor C directly fed to the stripping zone in reactor-stripper A is such that a normal or higher than normal stripping efficiency can be achieved, taking into account the amount of heat available for the stripping treatment, so that after expansion in expansion valve 6, the resulting urea product stream can be further processed in a known manner together with that portion of the urea product stream leaving heater-decomposer D. In this case, the total amount of ammonia needed in the process is fed into the reaction zone of stripper-reactor A. If necessary, however, a portion of the fresh ammonia can be fed into carbamate condenser B through line 39 and expansion valve 40.

In practicing the embodiment illustrated in FIG. 2 as described above, a reduction in high-pressure steam consumption (25 bar) of about 20–60 percent can be achieved relative to the process described in European Chemical News Urea Supplement and discussed above, again the precise steam savings depending upon the process conditions chosen.

Figure 3:
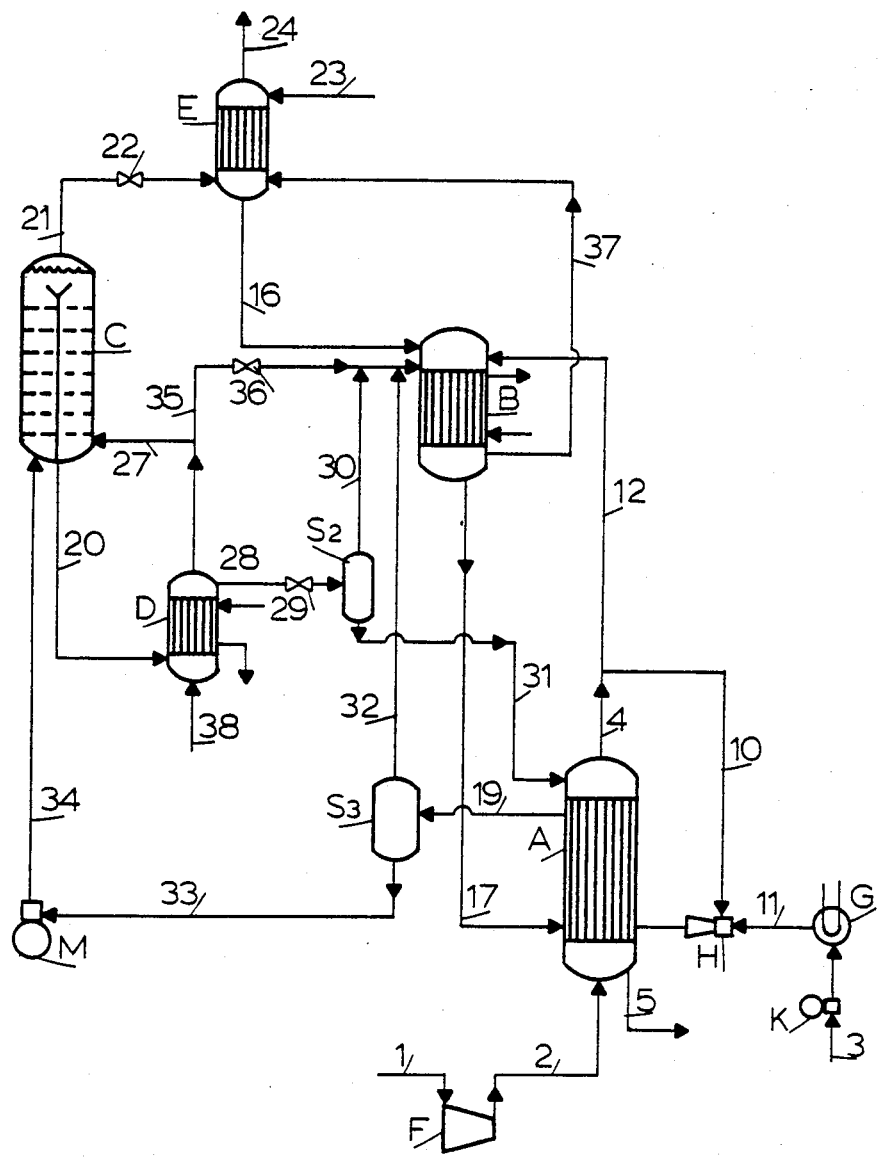
FIG. 3 illustrates another embodiment of the invention wherein a first minor portion of the carbamate present in the urea synthesis solution is decomposed and expelled by heating with steam, and a major portion of the remaining ammonium carbamate still present in the urea solution is stripped with the aid of heat derived from heat exchange with the reaction zone.

In the embodiment illustrated in FIG. 3, the urea solution discharged from after-reactor C is first treated in heater-decomposer D with steam to decompose an initial quantity of unconverted ammonium carbamate. In this embodiment, heater-decomposer D is schematically shown as a cocurrent heater-decomposer, but a countercurrent heater-decomposer can be used as well. To protect the materials of construction from corrosion, air or an oxygen-containing inert gas can be supplied to heater-decomposer D through line 38 for passivation.

In heater-decomposer D, a portion of the ammonium carbamate is decomposed and removed from the urea synthesis stream and a portion of the gas mixture thus formed is returned through line 27 to after-reactor C. The remaining portion of this gas mixture is discharged to carbamate condenser B via line 35 and expansion valve 36. In this embodiment, after-reactor C is maintained at a higher pressure than the reaction zone of reactor-stripper A, the latter being maintained at a pressure of 125–200 bar, for example, 140 bar, and the after-reactor being maintained at a pressure of 160–250 bar, for example, 190 bar.

The urea product stream leaving heater-decomposer D, still containing a portion of ammonium carbamate, is passed via line 28 and through expansion valve 29 into gas-liquid separator $S_2$, which operates at the pressure of the stripping zone of reactor-stripper A, wherein the gas mixture evolved from the expansion is separated from the urea product stream and introduced into carbamate condenser B through line 30. The remaining urea solution, still containing a portion of the non-converted carbamate and free ammonia, is introduced via line 31 into the stripping zone of reactor-stripper A. Here, substantially all of the ammonium carbamate still present in the urea solution is decomposed with the aid of heat transferred from the reaction zone so that the urea solution discharged through line 5 has only a small amount of carbamate remaining, which can be removed in a known manner.

In this embodiment, the gas mixture containing non-condensed inert components leaving the reaction zone of reactor-stripper A through line 19 is separated from the urea solution in gas-liquid separator $S_3$, and the remaining urea solution is led via line 33 to pump M whereby it is brought up to the pressure of after-reactor C is introduced therein via line 34. The gas mixture withdrawn from gas-liquid separator $S_3$ is led via line 32 to carbamate condenser B wherein the ammonia and carbon dioxide are condensed out. The inert-containing gases from carbamate condenser B, via line 37, as well as the inert gases from after-reactor C, via line 21 and expansion valve 22, are discharged to scrubber E in which ammonia and carbon dioxide still present in the inert gases are recovered by scrubbing with a dilute carbamate solution supplied through line 23.

In the embodiment illustrated in FIG. 3 and described above, the urea solution from the reaction zone of reactor-stripper A continues to react in after-reactor C at a higher pressure than in the reaction zone, so that a higher degree of conversion of ammonium carbamate to urea is achieved, and thus a smaller amount of carbamate need be decomposed. It is also possible, however, to carry out the after-reaction at the same pressure used in the reaction zone. Although a larger quantity of carbamate will then have to be decomposed there is the advantage that separators $S_2$ and $S_3$ and pump M, together with associated lines, valves, and measuring and control instrumentation, can be dispensed with.

EXAMPLE

Urea was prepared in accordance with the process illustrated in FIG. 2 as described above. For each tonne of urea to be produced, 567 kg of ammonia at a temperature of 120° C. is fed to the reaction zone of reactor-stripper A through ammonia pump K and ammonia heater G, and 733 kg carbon dioxide and 29 kg of inert gases (primarily air) are fed to the stripping zone of reactor-stripper A through carbon dioxide compressor F. The pressure in both zones of reactor-stripper A is maintained at 240 bar. The reaction zone is additionally fed, via ejector H, with a gas mixture consisting of 212 kg ammonia, 651 carbon dioxide, 13 kg water, and 23 kg inert gas and, via carbamate pump L, with 1584 kg of a carbamate solution consisting of 818 kg ammonia, 562 kg carbon dioxide, and 204 kg water. The volume of the reaction zone, and consequently the residence time, is such that, with the pressure of 240 bar therein maintained and the temperature of about 200° C. associated with this pressure, a gas-liquid mixture is formed in which the liquid phase is composed of 800 kg urea, 1009 kg ammonia, 524 kg carbon dioxide, and 449 kg water, and the gas phase consists of 135 kg ammonia, 102 kg carbon dioxide, 8 kg water vapor, and 23 kg of inert components.

The quantity of urea formed in the reaction zone is about 76% of the quantity of urea that would be obtained if the conversion would be allowed to proceed to equilibrium.

This gas-liquid mixture is introduced into after-reactor C via line 19 for further reaction wherein a urea synthesis solution consisting of 1000 kg urea, 913 kg ammonia, 393 kg carbon dioxide, and 510 kg of water is formed. About 32.5 wt.% of this urea synthesis solution is sent to the stripping zone of reactor-stripper A via line 20, while the remaining portion, after expansion to a pressure of 140 bar, is fed to gas-liquid separator $S_1$.

In the stripping zone, a major portion of the carbamate present in the urea solution fed thereto is decomposed. The ammonia and carbon dioxide thereby released are expelled by stripping with carbon dioxide fed into the stripping zone through line 2, resulting in a discharge of 1124 kg of a gas mixture through line 4 consisting of 265 kg ammonia, 814 kg carbon dioxide, 16 kg water vapor, and 29 kg inert gas. About 80 wt.% of this gas mixture is introduced into the reaction zone of reactor-stripper A via line 10, and the remaining portion, after expansion to 140 bar, is sent to carbamate condenser B. The remaining urea product stream discharged from the stripping zone of reactor-stripper A contains, in addition to 325 kg urea and 150 kg water, only 32 kg ammonia and 47 kg carbon dioxide.

In gas-liquid separator $S_1$, 184 kg of gas mixture evolved from the expansion of the urea synthesis solution from after-reactor C from 240 to 140 bar is separated from 1716 kg of remaining urea product solution. This urea product solution, consisting of 675 kg urea, 494 kg ammonia, and 213 kg carbon dioxide, the balance being water, is heated to 210° C. in co-current heater-decomposer D resulting in the decomposition of an additional quantity of ammonium carbamate, and the evolution of ammonia and carbon dioxide in gaseous form. The resulting gas mixture contains 268 kg ammonia, 163 kg carbon dioxide and 30 kg of water. The remaining urea product solution leaving heater-decomposer D consists of 675 kg urea, 304 kg water, 226 kg ammonia, and 50 kg carbon dioxide. The heat required for the decomposition and removal of off-gases in heater-decomposer D is provided by 354 kg of superheated steam having a temperature of about 300° C. and a pressure of 26 bar. From the condensation taking place in carbamate condenser B of the gas mixtures supplied thereto from the stripping zone, gas-liquid separator $S_1$ and heater-decomposer D, sufficient heat is released to form 550 kg of saturated steam of 3.5 bar.

We claim:

1. Process for the preparation of urea from ammonia and carbon dioxide at an elevated temperature and pressure having a reaction zone and a stripping zone wherein in said reaction zone, carbon dioxide and a portion of said ammonia are converted to ammonium carbamate, and a portion of said ammonium carbamate is converted to urea to form a reaction zone effluent containing product urea, unconverted ammonium carbamate, and excess ammonia, said conversions resulting in a net formation of heat, and in said stripping zone, a urea product stream containing unconverted ammonium carbamate is heated to decompose at least a portion of said ammonium carbamate by heat exchange with said reaction zone, and stripped with carbon dioxide to remove gaseous ammonia and carbon dioxide thus formed from said urea product stream, characterized in that said reaction zone is maintained at a pressure of at least 20 bar higher than the pressure in said stripping zone and the conversion of ammonium carbamate to urea in said reaction zone is continued until the quantity of urea formed is at least 50 percent of that quantity of urea that would be obtained at equilibrium under the reaction conditions present in said reaction zone.

2. Process according to claim 1, characterized in that the conversion of ammonium carbamate into urea in said reaction zone is continued until the quantity of urea formed is at least 70 percent of that quantity of urea that would be obtained at equilibrium under the reaction conditions present in said reaction zone.

3. Process according to claim 1 or 2, characterized in that the contents of said reaction zone are intensively mixed.

4. Process according to claim 3, characterized in that said reaction and stripping zones are within a vertical tube and shell heat exchanger, said stripping zone being within the tubes of said heat exchanger and said reaction zone being within the shell of said heat exchanger, and wherein the temperature differential between the top and bottom of said reaction zone is limited to at most 5° C.

5. Process according to claim 4, characterized in that the temperature differential between the top and bottom of said reaction zone is limited to at most 2° C.

6. Process according to claim 1, characterized in that said reaction zone is maintained at a pressure in the range of between about 125 and 250 bar and at a temperature in the range of between about 170° and 205° C.

7. Process according to claim 1 characterized in that pressure in said reaction zone is 40–60 bar higher than the pressure within said stripping zone.

8. Process according to claim 1, characterized in that the reaction zone effluent is introduced into an after-reaction zone wherein an additional portion of ammonium carbamate is converted to urea to form a urea product stream containing urea, in a quantity at least 90 percent of the quantity of urea that would be formed at equilibrium under the conditions prevailing in said after-reaction zone.

9. Process according to claim 8, characterized in that the pressure in said after-reaction zone is higher than the pressure in said reaction zone.

10. Process according to claim 9, characterized in that a pressure of between about 125 and 200 bar is maintained in said reaction zone, and a pressure of between about 160 and 250 bar is maintained in said after-reaction zone.

11. Process according to claim 8, characterized in that the urea product stream from said after-reaction zone is heated to a temperature of between about 180° and 210° C. whereby a portion of said unconverted ammonium carbamate is decomposed, the gas mixture thereby evolved is separated from the residual product urea stream, and the residual urea product stream still containing unconverted ammonium carbamate and free ammonia is introduced into said stripping zone.

12. Process according to claim 1, characterized in that the urea product stream from said stripping zone is introduced into a second stripping zone wherein additional ammonium carbamate is decomposed and removed from the urea product stream.

13. Process according to claim 8, characterized in that only a portion of the urea product stream from said after-reaction zone is introduced into said stripping zone, and a remaining portion of the urea product stream from said after-reaction zone is introduced into a second stripping zone wherein ammonium carbamate is decomposed.

14. Process according to claim 12, characterized in that said second stripping zone is maintained at a lower pressure than said stripping zone.

* * * * *